(12) United States Patent
Venderbosch et al.

(10) Patent No.: US 9,193,679 B2
(45) Date of Patent: Nov. 24, 2015

(54) PROCESS FOR DEPLOYMERIZING POLYSULFIDES AND THE PREPARATION OF BIS-MERCAPTO-DIETHERS

(71) Applicant: Akzo Nobel Chemicals International B.V., Amersfoort (NL)

(72) Inventors: Rudolf Anthonius Maria Venderbosch, Duiven (NL); Hendrika Petronella Maria Verlaan-Hooft, Soest (NL); Auke Gerardus Talma, Bathmen (NL); Olaf Klobes, Greiz (DE); Ralf Tatas, Alsdorf (DE); Hendrik Jan Vos, Apeldoorn (NL)

(73) Assignee: AKZO NOBEL CHEMICALS INTERNATIONAL B.V., Amersfoort (NL)

(*) Notice: Subject to any disclaimer, the term of this patent is extended or adjusted under 35 U.S.C. 154(b) by 0 days.

(21) Appl. No.: 14/644,342

(22) Filed: Mar. 11, 2015

(65) Prior Publication Data

US 2015/0183733 A1 Jul. 2, 2015

Related U.S. Application Data

(62) Division of application No. 13/634,932, filed as application No. PCT/EP2011/053758 on Mar. 14, 2011, now Pat. No. 9,006,492.

(60) Provisional application No. 61/317,842, filed on Mar. 26, 2010.

(30) Foreign Application Priority Data

Mar. 17, 2010 (EP) .................................. 10156724

(51) Int. Cl.
| | | |
|---|---|---|
| C08G 75/00 | (2006.01) | |
| C07C 319/06 | (2006.01) | |
| C08G 75/14 | (2006.01) | |
| C08L 81/04 | (2006.01) | |
| C07C 319/28 | (2006.01) | |

(52) U.S. Cl.
CPC ............. *C07C 319/06* (2013.01); *C07C 319/28* (2013.01); *C08G 75/14* (2013.01); *C08L 81/04* (2013.01)

(58) Field of Classification Search
CPC ...................................................... C08G 75/00
USPC ............................................................ 568/62
See application file for complete search history.

(56) References Cited

U.S. PATENT DOCUMENTS

| | | | |
|---|---|---|---|
| 2,466,963 A | 4/1949 | Patrick et al. | |
| 2,548,718 A | 4/1951 | George, Jr. et al. | |
| 2,676,165 A | 4/1954 | Fettes | |
| 3,294,760 A | 12/1966 | Hay | |
| 3,484,418 A | 12/1969 | Vandenberg | |
| 3,522,312 A | 7/1970 | Reece | |
| 3,523,985 A | 8/1970 | Marrs | |
| 4,623,711 A | 11/1986 | Morris et al. | |
| 9,006,492 B2 * | 4/2015 | Venderbosch et al. | 568/62 |

FOREIGN PATENT DOCUMENTS

| | | | | |
|---|---|---|---|---|
| DE | 737334 C | | 7/1943 | |
| DE | 737334 C | * | 7/1943 | ............ C07C 319/06 |
| EP | 1044936 A2 | | 10/2000 | |
| WO | WO 87/01724 A1 | | 3/1987 | |
| WO | WO 2006037442 A1 | | 4/2006 | |
| WO | WO 2007101819 A1 | | 9/2007 | |

OTHER PUBLICATIONS

Spielberger et al., English version of German Patent DE737334C, Jul. 1943; Human Translation 7 pages.*
English language translation of Office Action dated Jun. 5, 2013 for corresponding Chinese Patent Application No. 201180013180.1.
English Abstract of E. Emilitri et al., New poly(amidoamine)s containing disulfide linkages in their main chain, J. Polymer Sci, Part A: Polym. Chem. (2005), 43(7), 1404-16.
English Abstract of M.E. Tenc-Popovic et al., Synthesis of disulfide polymers of low molecular weight by repeated depolymerization, J. Polymer Sci. Part A-1:Polym. Chem. 1972.
M.A. Walters et al., The formation of disulfides by the [Fe(nta)Cl2]2-catalyzed air oxidation of thiols and dithiols, Inorg. Chim. Acta 359 (2006) 3996-4000, US.
I. Bereczki er al., Template effect of vancomycin . . . : A MALDI-TOF MS and solvent effect study, Carbohydr. Polym. 73 (2008)1-7, HU.
International Search Report dated Apr. 20, 2011 for PCT Application No. PCT/EP2011/053758.
European Search Report dated Jul. 27, 2010 for EP Application No. 10 15 6724.
Machine Translation of DE 737334 C, Jul. 10, 1943.

* cited by examiner

*Primary Examiner* — Porfirio Nazario Gonzalez
*Assistant Examiner* — Kofi Adzamli
(74) *Attorney, Agent, or Firm* — Sandra B. Weiss

(57) ABSTRACT

The invention related to a process for the preparation of a bismercaptodiether by reacting a polysulfide with a monothiol in the presence of a base and to a process for the depolymerization of a polysulfide by reacting said polysulfide with a monothiol in the presence of a base.

These processes enable the preparation of bismercaptodiethers without inorganic salt formation.

17 Claims, 1 Drawing Sheet

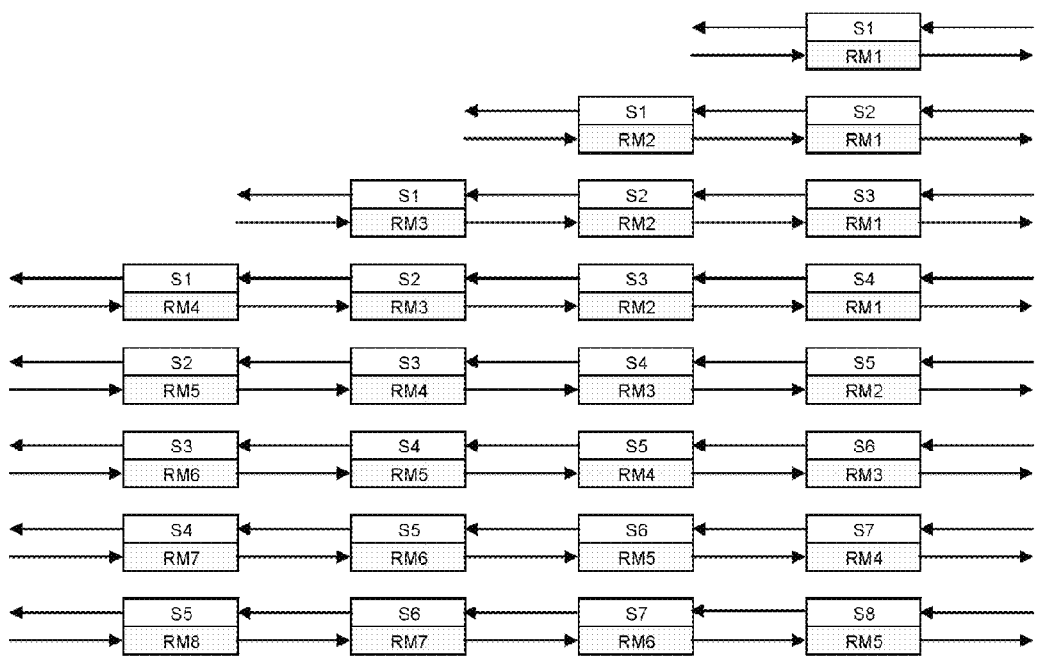

PROCESS FOR DEPLOYMERIZING POLYSULFIDES AND THE PREPARATION OF BIS-MERCAPTO-DIETHERS

CROSS-REFERENCE TO RELATED APPLICATIONS

This application is a divisional of U.S. patent application Ser. No. 13/634,932, filed on Oct. 19, 2012, which is national stage filing under 35 U.S.C. §371 of PCT/EP2011/053758, filed on Mar. 14, 2011, which claims priority to European Patent Application No. 10156724.6, filed on Mar. 17, 2010, and Provisional Application No. 61/317,842, filed on Mar. 26, 2010, the contents of which are each incorporated herein by references in their entirety.

Polysulfides are a class of polymers with alternating chains of several sulfur atoms and hydrocarbons. The general formula for the repeating unit is $-[R-S_x]_n-$, where x indicates the number of sulfur atoms, n indicates the number of repeating units, and R is an organic radical. Cured polysulfide polymers are resistant to ageing and weathering, are highly elastic from −40 to +120° C., and they offer an outstanding chemical resistance, especially against oil and fuel. Because of their properties, these materials find use as base polymer for sealants applied to fill the joints in pavement, insulation glass units, and aircraft structures.

Polysulfide polymers are conventionally synthesized by condensation polymerization reactions between organic dihalides and alkali metal salts of polysulfide anions:

$$n\text{Na}_2\text{S}_x + n\text{ClCH}_2\text{CH}_2\text{OCH}_2\text{OCH}_2\text{CH}_2\text{Cl} \rightarrow [\text{CH}_2\text{CH}_2\text{OCH}_2\text{OCH}_2\text{CH}_2\text{S}_x]_n + 2n\text{NaCl}$$

Dihalides used in this condensation polymerization are dichloroalkanes, such as 1,2-dichloroethane, bis-(2-chloroethyl) formal ($\text{ClCH}_2\text{CH}_2\text{OCH}_2\text{OCH}_2\text{CH}_2\text{Cl}$), and 1,3-dichloropropane. The obtained macromolecules are usually reduced to the required chain length by reductive splitting. The split disulfide groups are converted into reactive terminal thiol groups.

The above process produces salt as by-product. Salt wastes are evidently undesired, resulting in a search for salt-free production processes.

A salt-free process is presented in US 2007/0249860, which discloses a process for the preparation of hydroxyalkyl-terminated polysulfides by reacting monomeric hydroxyalkyl-terminated polysulfides, in particular dithioglycols, with formaldehyde in the presence of an acid:

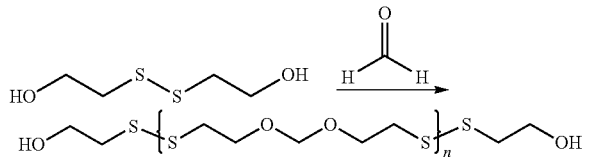

The resulting hydroxyalkyl-terminated polysulfides, however, cannot be applied in systems that are based on oxidative curing methods. This in contrast to mercapto-terminated polysulfides, which are far more reactive under these conditions.

Preparing mercapto-terminated polysulfides by transforming the hydroxy end groups of the above polymers into mercapto end groups in high yields seems to be troublesome, if possible at all. Especially when taking into account that high conversions have to be realized and that the risk of chain scission is high. Furthermore, the transformation may involve the formation of inorganic salts, which have to be washed out.

Another way to prepare mercapto-terminated polysulfides is by polymerizing bismercaptodiethers, i.e. $\text{HS}-\text{R}^1-\text{O}-\text{C}(\text{R}^2)-\text{O}-\text{R}^1-\text{SH}$. This is known from e.g. U.S. Pat. No. 3,523,985. Although this polymerization reaction is salt-free, the preparation of the starting bismercaptodiether does involve the formation of salt. That is, according to conventional methods, bismercaptodiethers are prepared by first preparing a dihalogenide ether from a hydroxyhalogenide and formaldehyde, followed by transforming the dihalogenide-diether into a bismercaptodiether. This process thus leads to the formation of inorganic halide salts.

The object of the present invention is therefore to provide a process for the preparation of bismercaptodiethers that does not lead to the formation of inorganic salts.

The present invention therefore relates to a process for the preparation of a bismercaptodiether of formula (I)

$$\text{HS}-\text{R}^1-\text{O}-\text{C}(\text{R}^2)\text{H}-\text{O}-\text{R}^1-\text{SH} \qquad (I)$$

by reacting a polysulfide with a repeating unit of formula (II)

$$-[\text{S}-\text{R}^1-\text{O}-\text{C}(\text{R}^2)\text{H}-\text{O}-\text{R}^1-\text{S}]- \qquad (II)$$

with a monothiol of the formula $\text{R}^4-\text{SH}$ in the presence of a base.

In the above formulae, $\text{R}^1$ is a linear, branched, or cyclic alkylene group with 1 to 6 carbon atoms, or an arylene group and $\text{R}^2$ is hydrogen, a linear, branched, or cyclic alkyl group with 1 to 6 carbon atoms, or an aryl group; $\text{R}^1$ and $\text{R}^2$ may be optionally substituted with heteroatoms. $\text{R}^4$ is a linear, branched, or cyclic alkyl, aryl, or alkaryl group, optionally substituted with heteroatoms.

The invention also relates to a process for the depolymerization of a polysulfide with a repeating unit of formula (II) by reacting said polysulfide with a monothiol of the formula $\text{R}^4-\text{SH}$ in the presence of a base.

$\text{R}^1$ is a linear, branched, or cyclic alkylene group with 1 to 6 carbon atoms, or an arylene group, and may be substituted with heteroatoms. Examples of suitable $\text{R}^1$ groups are $-\text{CH}_2\text{CH}_2-$, $-\text{CH}(\text{CH}_3)-\text{CH}_2-$, $-\text{CH}_2-\text{CH}(\text{CH}_3)-$, $-\text{CH}_2\text{CH}_2\text{CH}_2-$, $-\text{CH}_2\text{CH}_2\text{CH}_2\text{CH}_2-$, $-\text{CH}_2\text{CH}_2\text{CH}_2\text{CH}_2\text{CH}_2-$, $-\text{CH}_2\text{CH}_2-\text{O}-\text{CH}_2\text{CH}_2-$, $-\text{CH}(\text{CH}_3)-\text{CH}_2-\text{O}-\text{CH}_2-\text{CH}(\text{CH}_3)-$, $-\text{CH}_2-\text{CH}(\text{CH}_3)-\text{O}-\text{CH}(\text{CH}_3)-\text{CH}_2-$, cyclohexyl, and phenyl. A most preferred $\text{R}^1$ group is $-\text{CH}_2\text{CH}_2-$.

$\text{R}^2$ is hydrogen, a linear, branched, or cyclic alkyl group with 1 to 6 carbon atoms, or an aryl group, and may be substituted with heteroatoms. Examples of suitable $\text{R}^2$ groups are $-\text{CH}_3$, $-\text{CH}_2-\text{CH}_3$, $-\text{CH}_2-\text{CH}_2-\text{CH}_3$, phenyl, and cylclohexyl. A most preferred $\text{R}^2$ group is hydrogen.

In one embodiment, the polysulfide has the following structure (formula III):

$$\text{R}^3-\text{S}-[\text{S}-\text{R}^1-\text{O}-\text{C}(\text{R}^2)\text{H}-\text{O}-\text{R}^1-\text{S}]_n-\text{S}-\text{R}^3 \qquad (III)$$

wherein $\text{R}^1$ and $\text{R}^2$ are as defined above, each $\text{R}^3$ is independently selected from $-\text{SH}$ and $-\text{OH}$ terminated alkyl, etheralkyl, aryl and alkaryl groups having 1 to 6 carbon atoms, and n ranges from 1 to 100.

Preferred $\text{R}^3$ groups are thioalkyl, etheralkyl, and hydroxyalkyl groups.

More preferably, $\text{R}^3$ is a hydroxyalkyl group, because hydroxy-terminated polysulfides can be prepared via a salt-free process, as disclosed in, for instance, US 2007/0249860. Furthermore, if both $\text{R}^3$ and $\text{R}^4$ are hydroxyalkyl groups, dihydroxy-terminated disulfide by-products are formed, which can be re-used to prepare hydroxyl terminated polysulfides according to formula (III). It is therefore preferred that $R^3$ and $R^4$ are both hydroxyalkyl groups. Even more preferably, $R^3=R^4$. Examples of suitable $R^3$ groups are hydroxyethyl, 3-hydroxypropyl, and 2-hydroxypropyl. Most preferably, $R^3$ is a hydroxyethyl group.

n is in the range 1 to 100, preferably 2 to 40, and most preferably 3 to 30.

In another embodiment, the repeating units are part of a network, which means that the polysulfide has the form of a network of interconnected polysulfide chains. At least 90 wt %, preferably at least 95 wt % of said network consists of the above-defined repeating units. Chains of repeating units are interconnected with linking units. Said linking units contain at least two and preferably at least three functional groups that are reactive with thiol or hydroxyl groups. These functional groups enable the linking units to connect individual polysulfide chains.

The polysulfide with the repeating unit of formula (II) is reacted with a monothiol—i.e. a compound containing only one thiol group—of the formula $R^4$—SH. The use of compounds with more than one thiol group will result in a very low yield of the bismercaptodiether of formula (I).

$R^4$ is a linear, branched, or cyclic alkyl, aryl, or alkaryl group, optionally substituted with heteroatoms. Examples of heteroatom-containing substituents are hydroxyl and ether groups. It will be clear that $R^4$ cannot contain an —SH group.

Examples of suitable $R^4$ groups are hydroxyethyl, 2-hydroxypropyl, and 3-hydroxypropyl.

In a preferred embodiment, the polysulfide has a structure according to formula (III) and $R^3$ and $R^4$ are equal.

A preferred monothiol with the formula $R^4$—SH is beta-mercaptoethanol (i.e. HO—$CH_2CH_2$—SH), because the use of this compound in the process of the present invention results in the formation of a dihydroxy-terminated disulfide—e.g. HO—$CH_2CH_2$—S—S—$CH_2CH_2$—OH— as by-product, which by-product can be re-used to prepare polysulfides with repeating units according to formula (II).

The monothiol and the polysulfide are preferably used in the process according to the present invention in molar ratios monothiol: repeating unit of at least 0.4:1, more preferably at least 1.6:1, and most preferably at least 2.0:1. This ratio is preferably not higher than 20:1, more preferably below 10:1, and most preferably below 8:1. For a complete depolymerization of the polysulfide with bismercaptodiether, the theoretically required molar amount of bismercaptoethanol is about twice the molar amount of repeating unit. Because equilibrium reactions are involved in the process, a higher ratio monothiol: repeating unit results in a higher concentration of bismercaptodiether. It is possible to increase the yield of bismercaptodiether by selective removal of one of the resulting products (either the bismercaptodiether or the byproduct) from the reaction mixture. Selective removal of the bismercaptodiether will result in an increase of its yield. In theory it is even possible to completely de-polymerize the polysulfide. Extraction, distillation, and membrane filtration are suitable methods for this removal. Extraction can be performed with an apolar solvent and is further outlined below. With such selective removal, lower monothiol: repeating unit ratios may suffice for high bismercaptodiether yields.

The process according to the invention has to be performed in the presence of a base. The pKa of said base is preferably higher, as determined in aqueous solution at 25° C., than the pKa of the monothiol. The base enables the formation of the anion of the monothiol, which allows said anion to react with the polysulfide forming the desired monomer. Hence, all bases which can form the anion of the monothiol are suitable in the present process. Obviously, acids cannot be used because they are not able to form the anion of the monothiol which is needed for the reaction with the disulfide bond.

Suitable bases are 1,4-diazabicyclo[2.2.2]octane, alkali metal compounds such as potassium t-butoxide, sodium methoxide, sodium ethoxide, sodium hydride, lithium hydroxide, sodium hydroxide, and potassium hydroxide, ammonia, primary amines such as benzylamine, secondary amines such as cyclohexylamine, and tertiary amines such as triethanolamine and triethylamine. The base is preferably used in the process according to the present invention in an amount of 0.01-5 wt % based on the total weight of the reaction mixture, more preferably 0.05-0.1 wt %, and most preferably 0.1-0.5 wt %.

The process according to the present invention is preferably performed at a temperature in the range 20-150° C., more preferably 20-120° C., and most preferably 20-100° C.

The process according to the invention may be performed in the presence of one or more organic solvents. Examples of such solvents are toluene, benzene, and xylene. In one embodiment, the process is performed in the absence of additional solvents, in which case the monothiol can function as solvent. If monothiol is desired to function as solvent, the molar ratio monothiol: repeating unit referred to above may be higher than 20:1.

Products that may result from the process according to the present invention include, apart from the bismercaptodiether of formula (I), oligomers thereof and by-products. The main by-products will be mixtures of $R^4$—S—S—$R^3$ and/or oligomers thereof.

In a preferred embodiment, the bismercaptodiether of formula (I) is isolated from the reaction mixture during the process of the present invention, thereby shifting the equilibrium towards said bismercaptodiether and increasing its yield. Examples of suitable separation methods are extraction, distillation, and membrane separation. Extraction is preferably conducted with apolar solvents like hexane, heptane, octane, nonane, decane, iso-octane, cyclohexane, methylcyclohexane, or petroleum ethers, which have a relatively high affinity for the bismercaptoether and a low affinity for the by-products. Extraction may be carried out at temperatures in the range 20-150° C.

In a more preferred embodiment, the process according to the present invention is conducted in a counter-current extraction column. Even more preferably, the process is continuously operated reactive counter-current extraction process. The counter-current extraction is preferably performed in more than one stage, preferably at least 4 stages, even more preferably at least 6 stages, and even more preferably at least 8 stages, and most preferably at least 10 stages. An example of a continuous multi-stage counter-current extraction column is a Kuhni tower. In such tower, the liquid/liquid interface is created and maintained by the dispersing action of an agitator. In the process according to the present invention, the extraction solvent will generally be the light phase and the reaction mixture will be the heavy phase, resulting in an extraction solvent flowing from bottom to top and a reaction mixture flowing from top to bottom. The bismercaptediether concentration in the extraction solvent will then increase while flowing from bottom to top.

It might be advantageous to add water to the reaction mixture. Water influences the solubility of the different compounds in the reaction mixture and may thereby influence the equilibrium and facilitate separation of the compounds. This is of particular advantage if the bismercaptodiether of formula (I) is isolated from the reaction mixture during the process of the present invention, for instance by extraction as described above.

The resulting bismercaptodiether of formula (I) can be used as such in sealants, adhesives, and coating compositions using, e.g., isocyanate cure, epoxy-resin cure, or acrylate resin cure.

Furthermore, it can suitably be used to make polysulfides, for instance SH-terminated polysulfides, in a salt-free process. Suitable processes are for instance disclosed by M. A. Walters et al., *Inorganica Chimica Acta* 359 (2006) 3996-4000 and I. Bereczki et al., Carbohydrate Polymers 37 (2008) 1-7, and in U.S. Pat. Nos. 3,294,760, 3,522,312, and 3,523,985. The bismercaptodiether can also be used to split extremely high molecular weight polysulfides to form lower molecular weight polysulfides, as described in for instance U.S. Pat. No. 4,623,711.

The polysulfides prepared from the bismercaptodiether have various applications, including the ones mentioned above for which the bismercaptodiether can be used, i.e. as binder in sealants, adhesives, and coating compositions, in isocyanate cure, in epoxy-resin cure, and in acrylated resin cure.

BRIEF DESCRIPTION OF THE DRAWING

FIG. 1 illustrates a process scheme for simulating a continuous multi-stage counter-current extraction, as further explained in the Examples.

EXAMPLES

Example 1

113.26 grams of beta-mercaptoethanol were added to 56.13 grams of a HTPS (hydroxyl-terminated polysulfide) polymer with a degree of polymerization of 16.

Potassium-t-butoxide (0.28 gram; 0.50 wt % based on HTPS) was added. The temperature was raised to 60° C. After 60 minutes, 360 grams of cyclohexane were added and the reaction was allowed to proceed for another 60 minutes. The cyclohexane upper layer was removed and to the remaining reaction mixture an additional amount of 360 grams of cyclohexane was added. After another 45 minutes at 60° C. the cyclohexane layer was again removed.

The cyclohexane layers were combined and the cyclohexane was evaporated, thereby yielding 42.30 grams of a mixture containing 23.69 grams (which corresponds to 44.1% conversion of HTPS into its monomers) of the desired bis(mercaptoethoxy)methane and 14.3 grams of mercaptoethanol.

Example 2

115.42 grams of beta-mercaptoethanol were added to 57.71 grams of a HTPS polymer with a degree of polymerization of 16. 0.28 gram (0.49 wt % based on HTPS) of potassium-t-butoxide was added. The temperature was raised to 80° C. After 35 minutes, 360 grams of cyclohexane were added and the reaction was allowed to proceed for another 45 minutes. The cyclohexane upper layer was removed and to the remaining reaction mixture an additional amount of 360 grams of cyclohexane was added. After another 45 minutes at 80° C. the cyclohexane layer was again removed.

The cyclohexane layers were combined and the cyclohexane was evaporated, thereby yielding 61.99 grams of a mixture containing 25.1 grams (which corresponds to 45.5% conversion of HTPS into its monomers) of the desired bis(mercaptoethoxy)methane and 27.4 grams of mercaptoethanol.

Example 3

This example is used to simulate the process of the invention in a 4-stage continuously operated counter-current extraction column.

In a first experiment 3-1, a reaction mixture containing 267.98 g of HTPS, 401.97 g of beta-mercaptoethanol and 1.33 g (0.5 wt % based on HTPS) of potassium-t-butoxide was prepared and allowed to react for 30 minutes at 60° C. Eight equal parts (coded RM1 to RM8) of 55 grams of this reaction mixture were contacted with 8 equal parts of 355.7 g cyclohexane (coded S1 to S8).

Reaction mixture RM1 was mixed for 20 minutes with solvent S1 at 60° C. (which was sufficient to approach chemical equilibrium closely). The resulting mixture was allowed to settle and separate into 2 liquid layers that were returned to the bottles with their unique sample number: RM 1 and S1.

In a second step, RM1 was mixed with fresh solvent S2, while the used solvent S1 was mixed with fresh reaction mixture RM2. After 20 minutes mixing at 60° C., the 2 liquids were separated and returned to the labelled bottles. The same was done for RM2 and S1.

This procedure was repeated according to the scheme of FIG. 1 from top to bottom, until a 4-stage counter-current process had been developed. Samples RM5-RM8 and S5-S8 were analyzed by gas-chromatography (after evaporating most of the cyclohexane).

In a second experiment 3-2, the procedure as described with experiment 3-1 was repeated with the exception that 22.5 g water was added to each of the reaction mixtures RM1 to RM8. Results are summarized in the table below.

|  | Exp. 3-1 | Exp. 3-2 |
|---|---|---|
| Conversion HTPS (%) | 75.8 | 83.0 |
| Fraction bis(mercaptoethoxy)methane in S5 | 98.2 | 98.6 |

These results show that a continuously operated counter-current extraction can be suitably used in the process of the present invention. The experiment is a proof of principle that the conversion obtained in a multi-stage counter-current process is significantly higher than in a single stage operation (examples 1 and 2). In principle it is possible to approach full conversion of HTPS into its monomers where all of the DMDH is obtained in the extract at an infinite number of stages.

The addition of water to the reaction mixture further improved the conversion of HTPS and the yield of bismercaptodiether.

The invention claimed is:
1. A process for the depolymerization of a polysulfide with the following repeating unit:

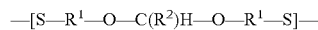

wherein $R^1$ is a linear, branched, or cyclic alkylene group with 1 to 6 carbon atoms, or an arylene group and $R^2$ is hydrogen, a linear, branched, or cyclic alkyl group with 1 to 6 carbon atoms, or an aryl group; $R^1$ and $R^2$ may be optionally substituted with heteroatoms,
which process comprises reacting said polysulfide with a monothiol of the formula $R^4$—SH, wherein $R^4$ is a linear or branched alkyl, aryl, or alkaryl group, optionally substituted with heteroatoms, in the presence of a base, at a temperature in the range of 20-150 C.

2. The process according to claim 1 wherein said polysulfide has the following structure:

$$R^3-S-[S-R^1-O-C(R^2)H-O-R^1-S]_n-S-R^3$$

wherein each $R^3$ is independently selected from —SH and —OH terminated alkyl, etheralkyl, aryl, and alkaryl groups having 1 to 6 carbon atoms, and n ranges from 1 to 100.

3. The process according to claim 2 wherein $R^3$ is an OH-terminated alkyl, etheralkyl, aryl, or alkaryl group with 1 to 6 carbon atoms.

4. The process according to claim 3 wherein $R^3$ is —CH$_2$CH$_2$OH.

5. The process according to claim 1 wherein said polysulfide is a network consisting for at least 90 wt % of said repeating units.

6. The process according to claim 1 wherein $R^2$ is hydrogen.

7. The process according to claim 1 wherein $R^1$ is —CH$_2$CH$_2$—.

8. The process according to claim 1 wherein $R^4$ is a hydroxy-terminated alkyl group.

9. The process according to claim 1 wherein said polysulfide reacts with said monothiol to form a bismercaptodiether that is separated from the reaction mixture during the reaction.

10. The process according to claim 9 wherein the bismercaptodiether is separated from the reaction mixture during the reaction by way of extraction.

11. The process according to claim 10 wherein the process is conducted as a multi-stage counter-current extraction process.

12. The process according to claim 11 wherein the multi-stage counter-current extraction process is operated continuously.

13. The process according to claim 11 wherein the number of stages is at least 4.

14. The process according to claim 1 wherein the reaction is performed in the presence of water.

15. A process for the preparation of a polysulfide comprising the steps of (i) depolymerizing a polysulfide according to the process of claim 1 and (ii) polymerizing the resulting product to form a polysulfide.

16. The process of claim 1 wherein $R^4$ is a linear or branched hydroxy-substituted alkyl group.

17. The process of claim 16 wherein $R^4$ is selected from hydroxyethyl, 2-hydroxypropyl, and 3-hydroxypropyl.

* * * * *